United States Patent [19]

Greene et al.

[11] Patent Number: 5,386,003

[45] Date of Patent: Jan. 31, 1995

[54] OIL ABSORBING POLYMERS

[75] Inventors: Carol J. Greene; Stephen H. Wu, both of Kingsport, Tenn.

[73] Assignee: Eastman Chemical Company, Kingsport, Tenn.

[21] Appl. No.: 33,198

[22] Filed: Mar. 15, 1993

[51] Int. Cl.$^6$ .................. C08G 63/02; C08G 63/68; C08L 77/00

[52] U.S. Cl. .................. 528/272; 528/275; 528/293; 528/254; 528/255; 528/300; 528/301; 528/335; 524/601; 524/602; 524/603

[58] Field of Search ............. 528/335, 272, 275, 293, 528/295, 294, 300, 301; 524/601, 602, 603

[56] References Cited

U.S. PATENT DOCUMENTS

| | | | |
|---|---|---|---|
| 3,546,008 | 12/1970 | Shields et al. | 117/138.8 |
| 3,734,874 | 5/1973 | Kibler et al. | 524/603 |
| 3,779,993 | 12/1973 | Kibler et al. | 528/295 |
| 4,233,196 | 11/1980 | Sublett | 524/602 |
| 4,335,220 | 6/1982 | Coney | 523/414 |
| 4,950,475 | 8/1990 | Vishnupad et al. | 424/83 |
| 4,960,814 | 10/1990 | Wu et al. | 524/315 |
| 4,992,508 | 2/1991 | Vishnupad et al. | 524/601 |
| 5,025,004 | 6/1991 | Wu et al. | 524/315 |
| 5,055,500 | 10/1991 | Peters et al. | 523/319 |
| 5,143,675 | 9/1992 | Yamamoto et al. | 264/171 |

FOREIGN PATENT DOCUMENTS 5310530 11/1993 Japan.

Primary Examiner—John Kight, III
Assistant Examiner—P. Hampton-Hightower
Attorney, Agent, or Firm—Bernard J. Graves, Jr.

[57] ABSTRACT

Water dispersible polyester polymers, polyesteramides polymers and blends of these polymers are dispersed in water and spray dried to form fine powders. In the solid state, these powders can absorb oils and/or diffuse ambient light, thereby resulting in the production of significant reduction in gloss and tack of lipids in cosmetic and personal care products when applied to ordinarily oily skin.

14 Claims, No Drawings

OIL ABSORBING POLYMERS

FIELD OF THE INVENTION

This invention belongs to the field of organic chemistry. In particular, it relates to finely powdered polyesters and polyesteramides which are dispersible in water and are useful as oil sequestering agents which alter the optical characteristics of a cosmetic or personal care formulation in which the rough texture of the powder serves to diffuse ambient light reflection.

BACKGROUND OF THE INVENTION

In cosmetic formulations and personal care products, mineral oil and petrolatum are commonly used as moisture barrier agents and carrier media for lipid soluble active ingredients. One disadvantage of these carrier media is that both materials are tacky and leave an undesirable greasy feel on the skin and often leave stains on clothing. We have found that certain water-dispersible polyesters can be made into powder form. When these compositions are incorporated into oily and greasy formulations, they minimize the disadvantages described above. Also, the presence of the water dispersible polyester makes it possible to remove the oily and greasy formulations from skin, clothing, and the like by washing with water or with water containing soap or detergents.

U.S. Pat. Nos. 3,779,993; 3,734,874 and 4,233,196 disclose the compositions of certain water dispersible polymers. They are described as linear, water-dissipatable, meltable polyesters or polyesteramides, having an inherent viscosity of at least 0.1 dL/g. The polymers are derived from monomer components which include dicarboxylic acid, hydroxycarboxylic acid, aminocarboxylic acid, aminoalcohol, glycol, diamine, or combinations of such monomer components wherein at least a part of the total of all monomer components is a poly(ethylene glycol) and at least one monomer component is substituted with one or more sulfonate metal salt groups. U.S. Pat. No. 3,546,008 discloses sizing compositions based on these water dispersible polymers and fibrous articles sized therewith.

U.S. Pat. No. 4,335,220 discloses aqueous compositions comprised of a water-dissipatable polyester or polyesteramide having dispersed therein a finely divided organic substance. Dry fine powdered water dispersible polyesters are not used.

It is known that certain water dispersible polymers can effectively complex water insoluble or non water dispersible organic and inorganic materials in an aqueous state. U.S. Pat. No. 5,143,675 describes a granulation process whereby a water dissipatable polymer is sprayed onto a fluidized bed of pigments.

U.S. Pat. No. 5,055,500 describes a melt extrusion process whereby a pigment/polymer blend is subjected to high shear to yield a product that is easily dispersed in water. The polymer described in this patent was a water dissipatable polyester polymer.

U.S. Pat. No. 4,992,508 describes the use of multivalent metal ions to cross-link aqueous dispersions of polyester or polyesteramide polymers. Cross-linked dispersions are then poured into a mold to form a cast. The material can serve as a carrier of active ingredients for cosmetic purposes or topical delivery of drugs from the molded film.

U.S. Pat. No. 4,950,475 describes the use of water dissipatable polyesters and polyesteramides used to make film-forming gels that contain high concentrations of humectants and emollients. The dispersion required high shear to disperse the aqueous and non-aqueous phase.

U.S. Pat. No. 4,335,220 describes water dispersions of certain water-dispersible polyesters as sequestering agents for water immiscible compounds such as sucrose acetate isobutyrate.

These references do not suggest the use of finely-powdered polyester or polyesteramide which can function, in the solid state, as sequestering agents for oily substances, which in the presence of oil can also absorb and hold water. There is also no mention of the ability of these polyester and polyesteramides powdered polymers to eliminate the tackiness of oil or to reduce the shine due to the roughness of the surface.

Aqueous dispersible polyesters (AQ polymers) are known to function as surface active agents which can disperse oils and water-insoluble substances in water. Water dispersible polyesters based on isophthalic acid, 5-sodiosulfoisophthalic acid, and glycols such as diethylene glycol are widely used in textile size and in ink formulations. The present invention, as described below, relates to water dispersible polyesters and polyesteramides in fine powder form which are readily dispersed in oil-based or water-based compositions. The presence of the polyesters and/or the polyesteramides significantly improves certain physical properties of the blends and facilitates the ready dispersion of water insoluble oils, greases, and waxes in water.

The present invention as described below provides novel compositions of aqueous polyesters polymers in a solid state as fine powder obtained by spray drying. The powdered polymers of the present invention control the shine of skin upon which the compositions are applied by diffusing ambient light.

SUMMARY OF THE INVENTION

The present invention provides water-dispersible polyester polymers, polyesteramides polymers and blends of these polymers which are spray dried to fine powders. In the solid state, these powders are useful for absorbing oils to produce a significant reduction in gloss and tack of lipids in cosmetic and personal care products.

DETAILED DESCRIPTION OF THE INVENTION

This invention provides compositions of solid fine powders of water dispersible polyester, polyesteramide and blends containing these polymers that can be used to sequester non water dispersible or water insoluble substances.

Thus, the present invention provides a water-dissipatable polyester and/or polyester-amide polymer powder having a particle size of about 0.1 to 100 microns obtained by spray-drying an aqueous dispersion of said powder.

In a preferred embodiment of the present invention, the polymer powder is a linear polymer having carbonyloxy linking groups in the linear molecular structure wherein up to 80% of the linking groups may be carbonylamido linking groups, the polymer having an inherent viscosity of at least about 0.1 measured in a 60/40 parts by weight solution of phenol/tetra-chloroethane at 25° C., and at a concentration of about 0.25 gram of polymer in 100 mL of the solvent, the polymer containing substantially equimolar proportions of acid equivalents (100 mole percent), the polymer comprising the reaction products of (a), (b), (c), and (d) from the following components or ester forming or ester amide forming derivatives thereof:

(a) isophthalic acid:
(b) from about 4 to about 25 mole percent, based on a total of all acid, hydroxyl and amino equivalents having equal to 20 mole percent, of at least one difunctional sulfomonomer containing at least one metal sulfonate group attached to aromatic nucleus wherein the functional groups are hydroxy, carboxyl, or amino;
(c) at least one difunctional reactant selected from a glycol or a mixture of a glycol or a mixture of a glycol and a diamine having two —NRH groups, the glycol containing two

—$CH_2$—OH groups of which at least 15 mole percent based on the total mole percent of hydroxy or hydroxy and amino equivalents, is a poly(ethylene glycol) having the structural formula:

H—(—$OCH_2$—$CH_2$—)$_n$—OH being an integer of between 2 and about 20; and
(d) from none to at least one difunctional reactant selected from a hydroxycarboxylic acid having one —$CR_2$—OH, an aminocarboxylic acid having one —NRH group, an amino-alcohol having one

—$CR_2$—OH group and one —NRH or mixtures thereof, wherein each R is an H atom or an alkyl group of 1 to 4 carbon atoms.

The compositions in this invention are desirable in many cosmetic applications, because they eliminate the tackiness of oily substances without adversely affecting the performance of the oily substance in the cosmetic applications. The polymer/oil dispersion can be washed off with soap and water.

Many polymers useful in this invention are described in U.S. Pat. Nos. 3,779,993, 3,546,008, 3,734,874, and 4,233,196, incorporated herein by reference. These polymers are generally prepared in melt phase polycondensation techniques well known in the art. The polymers as prepared are directly dispersed in hot water or extruded into rods and chopped into pellets. These pellets can later be dispersed in hot water if desired. Antiblocking agents can be added to the external surface of the polymer pellets to prevent agglomeration or sticking of the pellets in moist atmospheres.

Powders of polymers can be obtained by cryogenic grinding, precipitation from organic or aqueous solutions, or by spray drying. For the purpose of this invention, the powder size must be quite small and particular sizes obtained by cryogenic grinding or precipitation are generally too high. The preferred method of providing powders useful in this invention is comprised of the spray drying of water dispersions containing preferably about 25 to about 35 weight percent of the polyesters or polyesteramides. Preferred polymers have an inherent viscosity (measured in 60/40 phenol/tetrachloroethane solution) in the range of about 0.1 to about 2.0 and a glass transition temperature ($T_g$) of at least about 50° C. If the $T_g$ value of the polymer is less than about 50° C., the spray dried powder tends to stick or to agglomerate. Powders obtained by the spray drying method of this invention generally have particle sizes of about 0.1 to about 100 microns as measured by a Hagman gauge. Powders with particle sizes ranging from about 0.1 to about 40 microns are preferred.

The aqueous dispersions are preferably sprayed as a single polymer or as a blend of two or more water dispersible polyesters or polyesteramides. The water dispersible polymer may also be blended with water insoluble, a sparingly water-dispersible substance, or non-water dispersible substance. The sparingly water-dispersible substances or water-insoluble substances can be monoglycerides, vegetable oils, fatty acid esters or alcohols, zinc stearate, zinc oxide, iron oxides, mica magnesium stearate, calcium stearate and the like. Such blends generally contain 90 to 99.9 weight percent of the water dispersible polymer and 10 to 0.1 weight percent of the additive.

The preferred range is 95/5 to 99.9/0.1 water dispersible polymer/additive substance. Water dispersible polyesters or polyesteramides with $T_g$ less than 50° C. can be blended with other compatible polyesters or polyesteramides having as higher $T_g$ value to provide compositions which can be spray dried.

The amount of lipid substances such as monoglycerides, corn oil, mineral oil, waxes etc. directly affects $T_g$. Consequently, the amount of lipid added to the dispersion for spray drying is limited by the critical $T_{g\ value}$.

The polymer dispersions can be treated with other water-insoluble substances such as inorganic pigments such as $TiO_2$, mica, and iron oxides, lubricating agents such as zinc stearate, calcium stearate, magnesium stearate, and zinc oxide, but a co-surfactant is generally required to disperse these materials. As with the lipids, formulations containing the above must be at or above the critical $T_g$ value.

The fine powdered polyesters and polyesteramides may provide the following desirable characteristics:

1. A composition with a range of hydrophobic character due to the presence of the hydrophobic components.
2. Powders that can be combined with talc or other face powders that can control the face shine due to sebum.
3. A polymer powder that is easily dispersed in water.
4. Composition may be oil based in which the powder/oil blend is able to absorb a limited amount of moisture, yet retain its water resistant character.
5. An advantage of such a system is that the fine powder dispersed in oil will reduce the tack of that oil, and as previously stated, will absorb moisture.
6. The fine powders can adsorb oil, and then can be dispersed into water.
7. Fine powders of the present invention can be dispersed in water-based cosmetic formulations or personal care formulations to control the shine of oily skin.

Thus, as a further aspect of the present invention, there is provided a method for sequestering water-dissipatable or non water-dissipatable substances, which comprises blending said substance with a water-dissipatable polyester and/or polyester-amide polymer powder having a particle size of about 0.1 to 100 microns, obtained by spray-drying.

As a further aspect of the present invention, there is provided a cosmetic or personal care composition comprising (I) the polymer powder as described above, and (II) about 0.1 to about 5 weight percent of one or more lipid materials.

A process which can be used to make the powders is described in the following steps.

Dissipation of Polymer in Water

Millipore filtered water is pre-heated to a temperature range of 70° to 90° C. Pellets are added to the water as it is stirred, and the dispersion is continually stirred for 30 minutes to ensure complete dissolution of polymer. Blends of polyester made from polymer pellets may be dispersed together or blended with separately prepared dispersions. The hydrophobic properties of the blends can be altered by preparing a homogeneous blend or polymer/hydrophilic substance which may require mechanical means such as high shear from a Ross homogenizer (a rotator/stator) or a microfluidizer (a cavitation process). The dispersions are cooled to ambient temperature.

Spray Drying Procedure

Dispersions are spray dried in a four foot Anhydro Spray drier fitted with a nozzle atomizer. The dryer is warmed up to the inlet temperature then water is pumped through the dryer until the outlet temperature has stabilized within the desired temperature range. The outlet temperature is adjusted by increasing or decreasing the rate of water pumped into the dryer. The line is then changed from water to polymer dispersion. Drying parameters are:

| | |
|---|---|
| Air flow | 30 to 50 cfm |
| Air Inlet Temperature | 85-95° C. |
| Outlet Temperature | 40 to 45° C. |
| Atomizing Air | 20 to 25 psi |

The polymer dispersion is pumped to the spray dryer using a peristaltic pump at a rate of 29 g/minute. A free-flowing polymer powder is collected from the bottom of the spray dryer.

Compositions of Some Useful Polyester Polymers

| Polymer No. | IPA mole % | SIP mole % | DEG mole % | CHDM mole % | IV | $T_g$ |
|---|---|---|---|---|---|---|
| 1 | 89 | 11 | 100 | 0 | 0.42 | 29 |
| 2 | 89 | 11 | 78 | 22 | 0.36 | 38 |
| 3 | 82 | 18 | 54 | 46 | 0.33 | 55 |
| 4 | 91 | 9 | 25 | 75 | 0.36 | 60-65 |
| 5 | 80 | 20 | 11 (EG) | 89 | 0.1-0.3 | 88 |

IPA = Isophthalic acid, SIP = 5-Sodiosulfoisophthalic acid, DEG = Diethylene glycol, CHDM = 1,4,-cyclohexanedimethanol, and EG = Ethylene glycol.

Description of Lipids

In this invention, lipids may be dispersed into the aqueous dispersion and spray dried. The range of lipid that can be spray dried is for 0 to 10 percent of the polymer weight, with the most preferred concentration at 0 to 5 percent lipids. The lipids may be a liquid or solid at room temperature. The substances should have a low degree of polarity such that they are non-miscible with water. They should be non-reactive with water and the water-dispersible polyester polymer. The dispersion should have a low multivalent ion content. Organic substances which may be used in this invention include organic substances having a carbon chain length of greater than or equal to four, such a vegetable oils, mineral oil, phospholipids, esters of fatty acids and fatty alcohols, monoglycerides, silicone oils, and those which can be spray dried. Inorganic substances included in this invention are $TiO_2$, zinc oxide, mica, Zn stearate, and the like which are typically used in cosmetic applications and personal care applications.

The organic or inorganic substances may be added to the dispersion and blended by mechanical means such as in a Waring Blender, a microfludizer, or a Ross homogenizer.

The following examples will further illustrate the invention.

EXAMPLE 1

Polymer No. 4 in a water dispersion containing 30 weight percent solids is spray dried using the above described procedure to provide a free flowing white powder with particle size ranging from 0.1 to 30 microns. A total of 25 g of this white powder is stirred into 75 g of petrolatum to provide an opaque, white dispersion. This dispersion is rubbed onto an arm. This coating is colorless on the skin, feels less greasy than an area of skin coating with unmodified petrolatum and it is more easily removed by washing with soap and warm water.

Similarly good results are achieved using 5 weight percent and 50 weight percent of the Polymer No. 4 fine powder in the petrolatum.

EXAMPLE 2

Fine powder (1–28 microns) is prepared from Polymer No. 5 using the spray drying technique described above. A total of 25 g of this fine powder is stirred into 75 g of mineral oil to provide an opaque, milky dispersion. When applied to an area of skin, the greasy feel of the oil and the gloss from the oil are significantly reduced, but is colorless on the skin.

When the experiment is repeated using coarse, cryogenically ground powder from Polymer No. 5, the powder tends to separate from the oil and it does not absorb the oil well.

EXAMPLE 3

Aqueous dispersions (30 weight percent solids) of Polymer No. 1 and Polymer No. 5 are mixed to provide a dispersion containing a 1:3 ratio of Polymer 1: Polymer 5. This dispersion is spray dried to provide fine powder (1–40 microns). This powder in readily dispersed in mineral oil to provide opaque dispersions containing 1, 5, 20, 40 and 60 weight percent of the powder. Similarly good results are achieved in petrolatum and lanolin.

The powder is also readily dispersed in molten waxes much as paraffin, ceresine, candelilla, beeswax, and carnauba wax.

EXAMPLE 4

Powder (1–28 microns) is prepared from a 30 weight percent water dispersion of a polyesteramide ($T_g$ 90° C.) containing 80 mole% isophthalic acid, 20 mole% 5-sodiosulfoisophthalic acid, 84 mole% 1,4-cyclohexanedimethanol, 11 mole% ethylene glycol and 5 mole% 4-aminomethylcyclohexylmethanol. This fine powder is readily dispersed in mineral oil.

Similarly good results are achieved using fine powder from Polymer 3.

EXAMPLE 5

Fine powder (1–40 microns) is prepared from a blend of Polymer 2 and Polymer 4. The blend contains 10% Polymer 2 and 90% Polymer 4. This powder is readily dispersed in mineral oil.

EXAMPLE 6

Fine powder from Polymer 4 (1–40 microns) is stirred into warm (40°–50° C.) MARY KAY ™ extra emollient night cream to provide a dispersion containing 25 weight percent of Polymer 4. When cooled to room temperature, a smooth, evenly dispensed light pink cream is obtained. The cream is easily applied to skin and is less greasy than the unmodified cream. It is readily removed by washing with soap and water.

Similarly good results are achieved using 1, 10, and 50 weight percent concentrations of the fine powder.

Similarly good results are also achieved when 25 weight percent of this fine powder is dispersed in commercial sun tan lotions.

EXAMPLE 7

Fine powder (1–40 microns) of Polymer 4 is blended with $TiO_2$ powder to provide blends containing 10 weight percent $TiO_2$. This powder blend is readily dispersed in mineral oil and petrolatum to provide smooth dispersions containing 1 to 50 weight percent powder.

Similarly good results are achieved using Polymer 4 powder blends containing talc, zinc stearate, or calcium stearate.

The compositions are useful in a solid fine powder because of the oil absorbing property. The product compositions are useful in cosmetic, and personal care products.

EXAMPLE 8

The fine powder (1–40 microns, preferably </=15 microns)) of Polymer 4 is blended with commercially available face powder, Talc, nylon, or other commonly available products. Ratios of the ingredients preferably vary as follows: 0.1–50 weight percent AQ fine powder. The powder preferably contains Iron Oxide as the coloring agent. Further preferred are the loose face powders as opposed to the pressed powders.

We claim:

1. A powder comprising a water-dissipatable polyester and/or polyester-amide polymer powder having a particle size of about 0.1 to 100 microns and a $T_2$ of 50° C. or greater, said powder obtained by spray-drying an aqueous dispersion of said powder.

2. The polymer powder of claim 1, which is a water-dissipatable polyester.

3. The polymer powder of claim 1, which is a water-dissipatable polyester-amide.

4. The polymer of powder of claim 1, having an inherent viscosity of about 0.1 to 2.0 dL/g.

5. The polymer powder of claim 1, which is a linear polymer having carbonyloxy linking groups in the linear molecular structure wherein up to 80% of the linking groups may be carbonylamido linking groups, the polymer having an inherent viscosity of at least about 0.1 measured in a 60/40 parts by weight solution of phenol/tetrachloroethane at 25° C., and at a concentration of about 0.25 gram of polymer in 100mL of the solvent, the polymer containing substantially equimolar proportions of acid equivalents (100 mole percent), the polymer comprising the reaction products of (a), (b), (c), and (d) from the following components or ester forming or ester amide forming derivatives thereof:

(a) isophthalic acid;

(b) from about 4 to about 25 mole percent, based on a total of all acid, hydroxyl and amino equivalents having equal to 20 mole percent, of at least one difunctional sulfomonomer containing at least one metal sulfonate group attached to aromatic nucleus wherein the functional groups are hydroxy, carboxyl, or amino;

(c) at least one difunctional reactant selected from a glycol or a mixture of a glycol or a mixture of a glycol and a diamine having two —NRH groups, the glycol containing two $$—CH_2—OH$$

groups of which at least 15 mole percent based on the total mole percent of hydroxy or hydroxy and amino equivalents, is a poly(ethylene glycol) having the structural formula:

$$H—(—OCH_2—CH_2—)_n—OH$$

n being an integer of between 2 and about 20; and (d) from none to at least one difunctional reactant selected from a hydroxycarboxylic acid having one —$CR_2$—OH, an aminocarboxylic acid having one —NRH group, an amino-alcohol having one $$—CR_2—OH$$

group and one —NRH or mixtures thereof, wherein each R is H atom or an alkyl group of 1 to 4 carbon atoms.

6. The polymer powder of claim 1, further comprising about 0.1 to about 5 weight percent of one or more lipid materials.

7. The polymer powder of claim 1, wherein said powder is in a range of about 1 to 40 microns in diameter.

8. A method for sequestering water-dissipatable or non water-dissipatable substances, which comprises blending said substance with a water-dissipatable polyester and/or polyester-amide polymer powder having a particle size of about 0.1 to 100 microns and a $T_g$ of 50° C. or greater, said powder obtained by spray-drying an aqueous dispersion of said polymer powder.

9. The method of claim 8, wherein the polymer powder is a water-dissipatable polyester.

10. The method of claim 8, wherein the polymer powder which is a water-dissipatable polyester-amide.

11. The method of claim 8, wherein the polymer of powder has an inherent viscosity of about 0.1 to 2.0 dL/g.

12. The method of claim 8, wherein the polymer powder is a linear polymer having carbonyloxy linking groups in the linear molecular structure wherein up to 80% of the linking groups may be carbonylamido linking groups, the polymer having an inherent viscosity of at least about 0.1 measured in a 60/40 parts by weight solution of phenol/tetrachloroethane at 25° C., and at a concentration of about 0.25 gram of polymer in 100 mL of the solvent, the polymer containing substantially equimolar proportions of acid equivalents (100 mole percent), the polymer comprising the reaction products of (a), (b), (c), and (d) from the following components or ester forming or ester amide forming derivatives thereof:

(a) isophthalic acid;

(b) from about 4 to about 25 mole percent, based on a total of all acid, hydroxyl and amino equivalents having equal to 20 mole percent, of at least one difunctional sulfomonomer containing at least one metal sulfonate group attached to aromatic nucleus wherein the functional groups are hydroxy, carboxyl, or amino;

(c) at least one difunctional reactant selected from a glycol or a mixture of a glycol or a mixture of a glycol and a diamine having two —NRH groups, the glycol containing two

—CH$_2$—OH groups of which at least 15 mole percent based on the total mole percent of hydroxy or hydroxy and amino equivalents, is a poly(ethylene glycol) having the structural formula:

H—(—OCH$_2$—CH$_2$—)$_n$—OH n being an integer of between 2 and about 20; and (d) from none to at least one difunctional reactant selected from a hydroxycarboxylic acid having one —CR$_2$—OH, an aminocarboxylic acid having one —NRH group, an amino-alcohol having one

—CR$_2$—OH group and one —NRH or mixtures thereof, wherein each R is an H atom or an alkyl group of 1 to 4 carbon atoms.

13. The method of claim 8, wherein the polymer powder further comprises about 0.1 to about 5 weight percent of one or more lipid materials.

14. The method of claim 8, wherein the polymer powder is in a range of about 1 to 40 microns in diameter.

* * * * *